(12) United States Patent
Neilson et al.

(10) Patent No.: US 7,717,922 B2
(45) Date of Patent: May 18, 2010

(54) VACUUM SEALING DEVICE

(76) Inventors: Geoffrey James Neilson, Hillcrest Avenue, Epping, NSW 2121 (AU); Anthony Maloof, P.O. Box 155, Kingsford, NSW 2032 (AU)

( * ) Notice: Subject to any disclaimer, the term of this patent is extended or adjusted under 35 U.S.C. 154(b) by 654 days.

(21) Appl. No.: 10/489,156

(22) PCT Filed: Aug. 23, 2002

(86) PCT No.: PCT/AU02/01147

§ 371 (c)(1),
(2), (4) Date: Aug. 9, 2004

(87) PCT Pub. No.: WO03/022191

PCT Pub. Date: Mar. 20, 2003

(65) Prior Publication Data

US 2004/0260254 A1   Dec. 23, 2004

(30) Foreign Application Priority Data

Sep. 11, 2001  (AU) ................... PR 7709
Jan. 31, 2002  (AU) ................... PS 0336
Apr. 22, 2002  (AU) ................... PS 1901

(51) Int. Cl.
*A61F 9/00*  (2006.01)
(52) U.S. Cl. .................................. 606/107
(58) Field of Classification Search ............. 606/107, 606/166, 191; 604/19, 22, 27, 35, 521; 600/37, 600/201, 207, 233, 237, 236; 128/898; 623/6.11, 623/6.12, 6.18; 294/1.2
See application file for complete search history.

(56) References Cited

U.S. PATENT DOCUMENTS

| | | | | |
|---|---|---|---|---|
| 2,555,076 A | * | 5/1951 | Crossley | 606/107 |
| 3,074,407 A | * | 1/1963 | Moon et al. | 606/166 |
| 4,047,532 A | * | 9/1977 | Phillips et al. | 606/107 |
| 4,286,815 A | * | 9/1981 | Clark | 294/1.2 |
| 4,526,171 A | * | 7/1985 | Schachar | 606/166 |
| 4,619,259 A | * | 10/1986 | Graybill et al. | 606/166 |
| 4,688,570 A | * | 8/1987 | Kramer et al. | 606/166 |

(Continued)

FOREIGN PATENT DOCUMENTS

WO   WO 00/74574   12/2000

(Continued)

OTHER PUBLICATIONS

Derwent Abstract Accession No. 84-119809/19, SU 1034746 A (As UKR Physics Unst) Aug. 15, 1983, Abstract.

(Continued)

*Primary Examiner*—Julian W Woo
(74) *Attorney, Agent, or Firm*—Gottlieb, Rackman & Reisman, P.C.

(57) ABSTRACT

A vacuum sealing devices (10) used for surgical procedures, particularly on the eye. The device (10) comprises a flexible sleeve (11) which terminates in a platter (11*a*) having a sealing suction ring (12, 112, 212). The suction ring (12, 112, 212) couples the sleeve (11) to the body and isolates the surgical site from surrounding tissue. The sleeve (11) may be provided with a opening (22, 113) which allows instrumentation access through and incision such as a corneal incision (13).

26 Claims, 8 Drawing Sheets

U.S. PATENT DOCUMENTS

| | | | |
|---|---|---|---|
| 4,796,623 A * | 1/1989 | Krasner et al. | 606/166 |
| 5,108,412 A * | 4/1992 | Krumeich et al. | 606/166 |
| 5,727,569 A * | 3/1998 | Benetti et al. | 128/898 |
| 5,772,675 A | 6/1998 | Hellenkamp | |
| 6,042,539 A | 3/2000 | Harper et al. | |
| 6,063,021 A * | 5/2000 | Hossain et al. | 600/37 |
| 6,071,295 A * | 6/2000 | Takahashi | 606/191 |

FOREIGN PATENT DOCUMENTS

WO     WO 02/43632     6/2002

OTHER PUBLICATIONS

US-5,725,569, Mar. 17, 1998, Benetti et al., See International Search Report.

\* cited by examiner

VACUUM SEALING DEVICE

TECHNICAL FIELD

The invention relates to vacuum sealing devices and more particularly to a vacuum sealing device and methods for the delivery of solutions to body surfaces or cavities.

BACKGROUND ART

It is sometimes desirable, during the course of surgery, to isolate one part of the body from the rest. For example, it may be desirable to administer a chemically active or toxic substance to one part of the body without that substance contacting other parts of the body. In other instances, it may be advantageous to prevent secretions, infectious materials or contaminants from spreading outside of the locality of the area which is being operated on. The present invention addresses these issues and illustrates the benefits of isolating a surgical site by referring to the specific example of cataract surgery.

During cataract surgery, the human lens is removed from within the lens capsule and replaced by an artificial lens. This is performed by tearing a small hole in the anterior capsule (a capsulorhexis) and then destroying and removing the human lens by phacoemulsification. However, lens cortex and epithelial cells remain following the lens removal. Irrigation/aspiration is routinely used to remove the visible cortex remnants. It is unreasonable to expect all lens epithelial cells (LECs) which are bound to both the anterior and posterior capsule to be removed by this method.

LECs which remain within the capsule have been shown to mutate and grow over the posterior surface of the implanted intra-ocular lens (IOL) thus causing posterior capsule opacification (PCO). This complication of cataract surgery has historically occurred at a rate as high as 30%, however recent IOL designs have reduced this to around 2-5% at 2 years. It remains unclear what the longer term rates of PCO with these IOLs will be.

The current treatment for PCO is a posterior capsulotomy using a Yag laser. Although the complication associated with this procedure is small, the cost is significant and there is a risk of retinal detachment.

Current methods for reducing the rate of PCO include IOL design. It has been shown that a lens with sharp edges causes a barrier to LEC growth. However, lens capsule fibrosis occurs and these IOLs have been shown to cause vision problems particularly at night due to reflections from these edges.

It has been proposed that cytotoxic chemicals can be used to destroy these epithelial cells, however, there is a risk that these chemicals damage other intraocular structures.

Research is currently underway into using accommodating IOLs, and clear lens extraction for the correction of refractive errors. However, for these technologies to be successful chronically, the lens capsule must remain flexible and free of fibrosis.

Therefore, there is still a need for a device which overcomes the current problems associated with adequate capsule cleaning and LEC removal.

Accordingly there is provided a flexible sleeve which terminates in a suction ring. The sleeve has formed in it an opening through which surgical instruments may be inserted.

DISCLOSURE OF THE INVENTION

Accordingly there is provided a vacuum sealing device comprising a flexible vacuum platter having an underside. The underside has, around its periphery, a vacuum channel. A flexible sleeve is attached to and extends from an exterior surface of the platter. The sleeve has an interior which opens onto the underside.

The invention also provides a vacuum sealing device comprising a flexible sleeve which has a distal extremity which terminates in a suction channel. The suction channel is in fluid communication with a flexible suction tube.

In preferred embodiments, the device is particularly adapted to fit within a human pupil and therefore lends itself to various surgical procedures on the human eye.

In other embodiments, the vacuum channel further comprises a barrier which is located within the channel and which is attached to a wall inside the channel.

In other embodiments, a flexible suction tube is in fluid communication with the vacuum channel and is joined to or incorporated into the sleeve.

MODES FOR CARRYING OUT THE INVENTION

Figure 1:
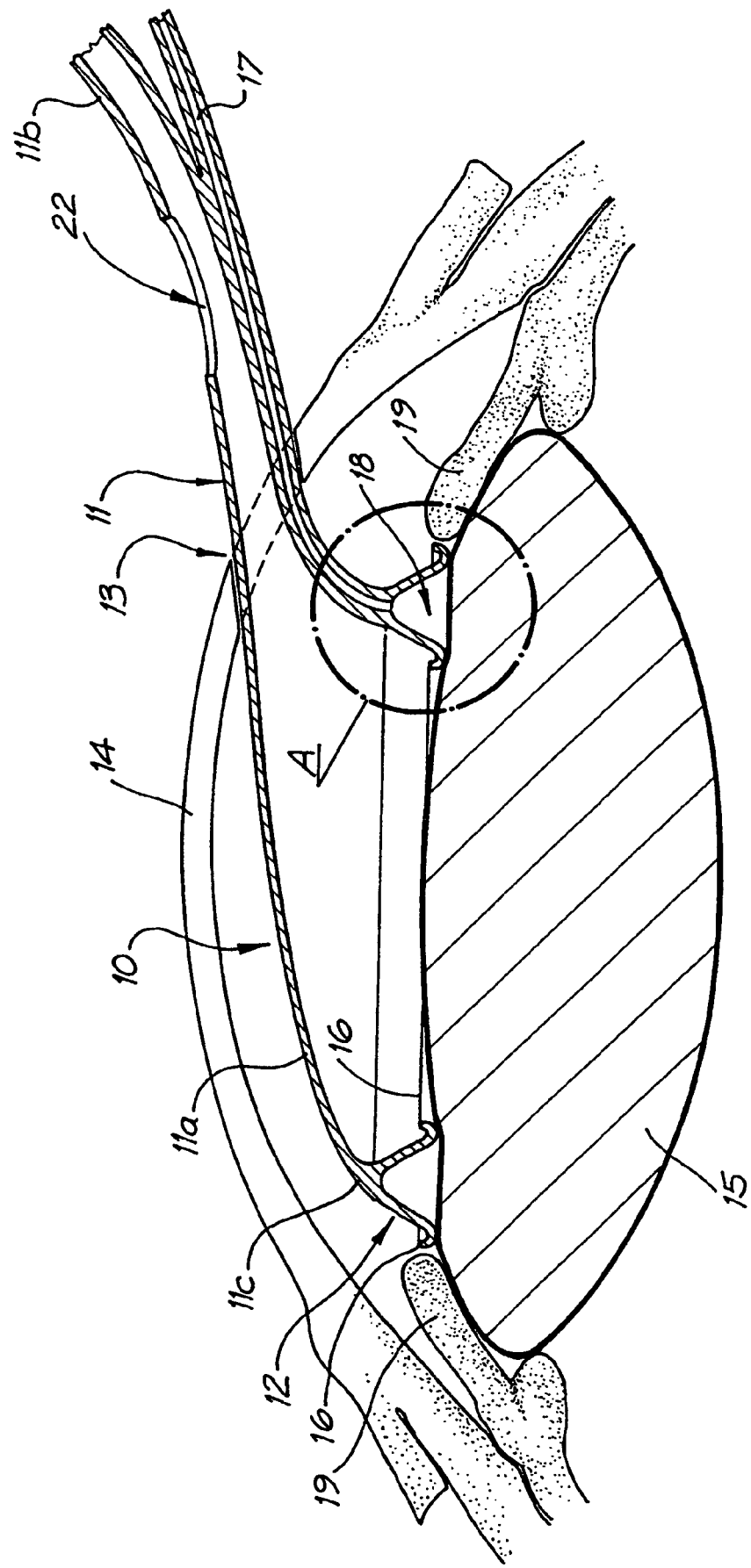
FIG. 1 is a schematic cross section of the present invention as applied to cataract surgery.

As shown in FIG. 1, a device according to one embodiment of the present invention comprises a flexible sleeve 11 having a distal extremity 11c which terminates in a vacuum platter having a suction ring 12 around its periphery on its underside which operates as a seal. In those embodiments intended for eye surgery where the device is sealed onto a lens capsule, the device is preferably foldable and flexible enough to be folded or rolled into a conformation for insertion through a corneal incision and the vacuum platter is sized to surround the capsulorhexis so as to provide a seal. The suction ring 12 has an inverted "U" shaped cross section. The sleeve 11 and suction ring 12 are preferably made from silicone or polyurethane or other soft and flexible materials. The internal surface of the sleeve may be coated with a slippery substance such as a hydrogel. The distal portion 11a of the sleeve 11 and suction ring 12 must be small enough and flexible enough to pass through the incision 13 in the cornea 14.

The suction ring 12 couples the sleeve 11 to the lens capsule 15. Accordingly, the distal edges 16 of the suction ring 12 are preferably blunted, radiused or otherwise enlarged to increase the contact area with the lens capsule and accordingly reduced the contact stress. The sleeve 11 incorporates or has attached to it a flexible suction tube 17. The flexible suction tube 17 communicates a suction or pressure from outside the eye to the interior 18 of the suction ring 12. The tube 17 is joined to the sleeve 11 or is formed integrally with it. It may be interior or exterior to the sleeve wall. The entire suction ring fits within the opening of the iris 19.

Figure 2:
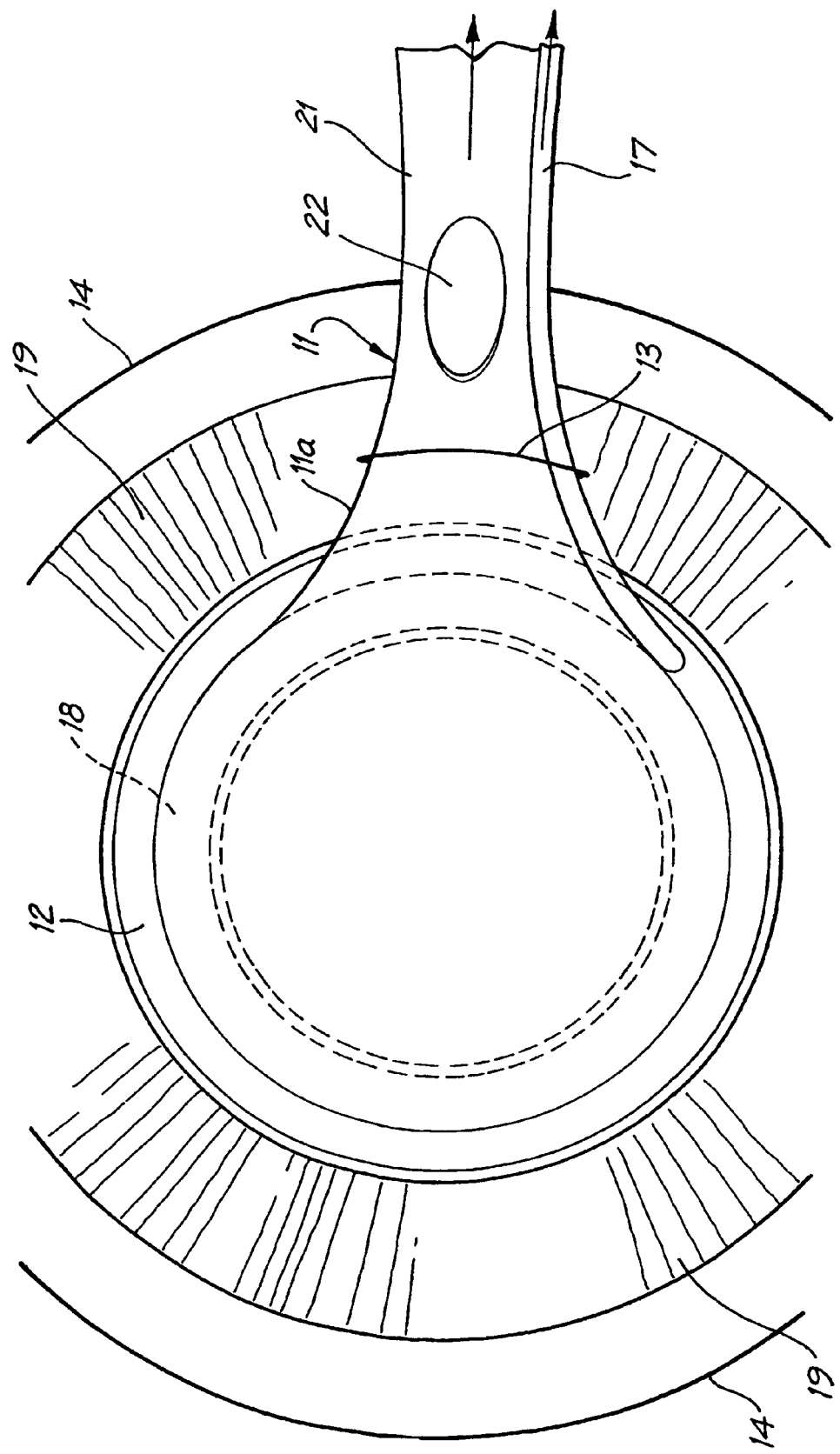
FIG. 2 is a schematic top plan view of the device detected in FIG. 1.

As shown in FIG. 2, the distal portion 11a of the sleeve 11 and suction ring 12 fit through the corneal incision 13 and the remainder of the sleeve 11 is external to the cornea 14. The external portion 21 of the sleeve 11 has an opening 22 formed in it. The opening 22 allows instrumentation access through the corneal incision 13. The portion of the sleeve 11 which passes through the corneal incision 13 and those areas immediately around it are referred to as the throat of the sleeve. In this instance, the throat has a maximum dimension of about 2.6 mm and in the area of the incision should be relatively flat to minimise wound distortion (see FIG. 3). The relatively flat configuration of the throat also provides, in use, some back pressure to the lens capsule, which back pressure allows the capsule to be inflated when fluid is introduced through the sleeve.

As shown in FIG. 3, the throat area 30 can assume various configurations. As shown in FIG. 3a, the throat 30 forms a flat ellipse with the suction tube 17 aligned along the long axis of the ellipse 31 of the throat 30. In this example, the suction tube 17 is joined to the exterior surface 32 of the sleeve 11. FIG. 3b illustrates an example in which a suction tube 17 and another tube 33 are carried on the exterior of the sleeve 11, both aligned with the long axis "X" of the ellipse 31 of the throat. FIG. 3c illustrates an embodiment where the suction tube 17 and the other tube 33 are located on or along the interior of the sleeve 11. In this example, the two tubes 17, 33 are located at opposite ends of the flat throat portion. In FIG. 3d, the suction tube 17 and the other tube 33 are adjacent to one another and located at the same side of the throat.

Figure 3A:
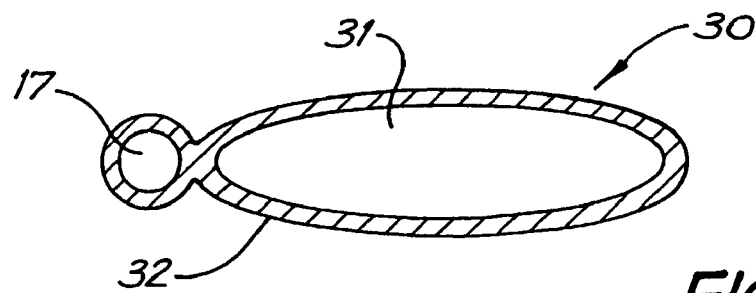
FIGS. 3a-3d are schematic cross sections of a sleeve of the type depicted in FIGS. 1 and 2.
Figure 3B:
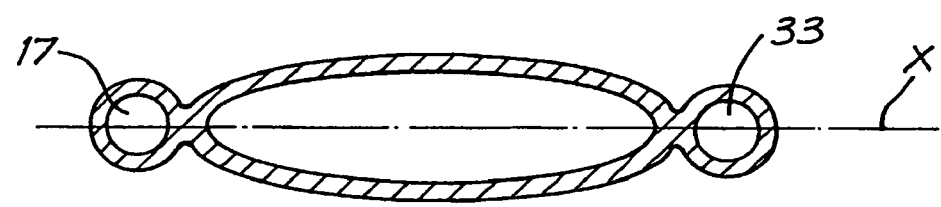
Figure 3C:
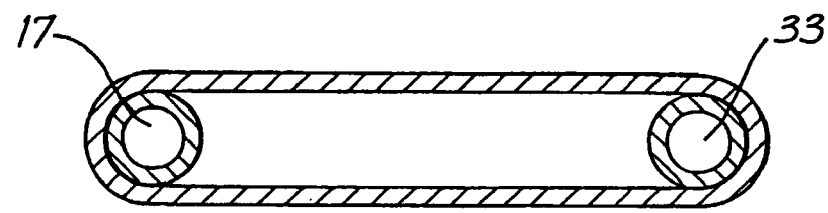
Figure 3D:
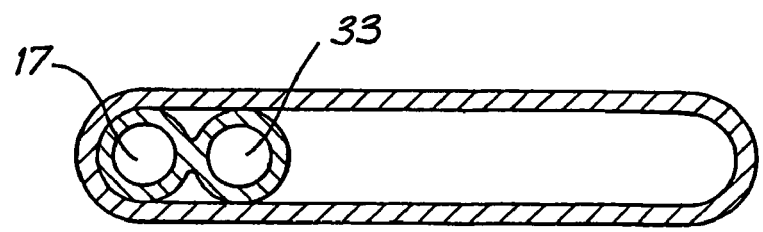

The other tube 33 referred to in FIGS. 3b to 3d can be used for any one of a variety of purposes. In one example, the other tube 33 serves as an alternate or secondary suction tube. In other embodiments, the other tube 33 can be used to either deliver or withdraw fluids (including gases if required) to the interior of the sleeve 11 and thereby into the lens capsule through the surgical opening in the capsule. In some embodiments, it will be preferable to terminate the tube 33 at a location diametrically opposite the point at which the suction tube 17 joins the suction ring 12. In this configuration, the tube 33 can serve as a guide for an insertion rod. Such a rod is inserted into the tube 33 for the purpose of manoeuvring the device 10 through the corneal incision 13 and into position on the capsule 15.

With respect to FIGS. 3a to 3d, it will be appreciated that the precise configuration of the sleeve and the throat section of the sleeve are such that the combination of cross section or configuration, wall thickness and sleeve geometry result in a slight but correct degree of back pressure into the lens capsule.

Figure 4:
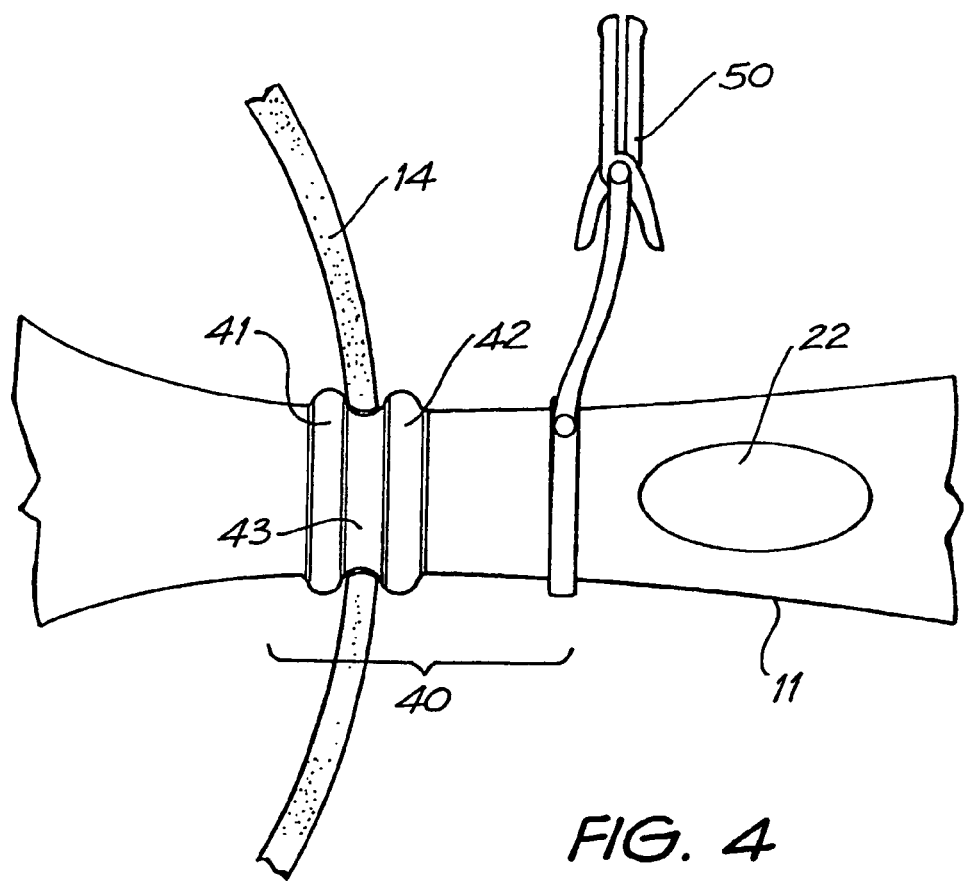
FIG. 4 is a schematic top plan view of a sleeve throat.

As shown in FIG. 4, the throat area 40 of the sleeve 11 passes through the cornea 14. In order to stabilise the interface between the sleeve 11 and the cornea 14, one or more stabilising ribs 41, 42 are provided around the exterior circumference of the sleeve 11. In one embodiment, a single circumferential rib is provided at a location between the instrument access opening 22 and the point on the sleeve 11 which passes through the cornea 14. The exterior rib 41 prevents the sleeve from being inserted further than the location of the rib 41. In another embodiment, a second and internal rib 42 is provided between the exterior rib 41 and the suction ring 12. A gap 43 is thereby defined between the internal and external ribs 42, 41, the cornea 14 fitting in the gap 43 between the two ribs 41, 42.

The sleeve 11 may be further stabilised with the provision of a stabilising clamp 50. The clamp 50 is affixed to the exterior of the sleeve 11 in the area between the instrument access opening 22 and the point where the sleeve enters the cornea 14.

With or without the provision of stabilising ribs 41, 42 or clamp 50, the instrument opening 22 which is formed on the proximal end of the sleeve 11 remains external to the cornea and allows instruments such as syringes and irrigation/aspiration cannulas to be inserted into the capsule without directly contacting the anterior chamber of the eye.

It will be appreciated that insertion devices such as forceps, a folder or injector system may be optionally provided to ease insertion of the device 10 into the interior chamber.

Figure 5:
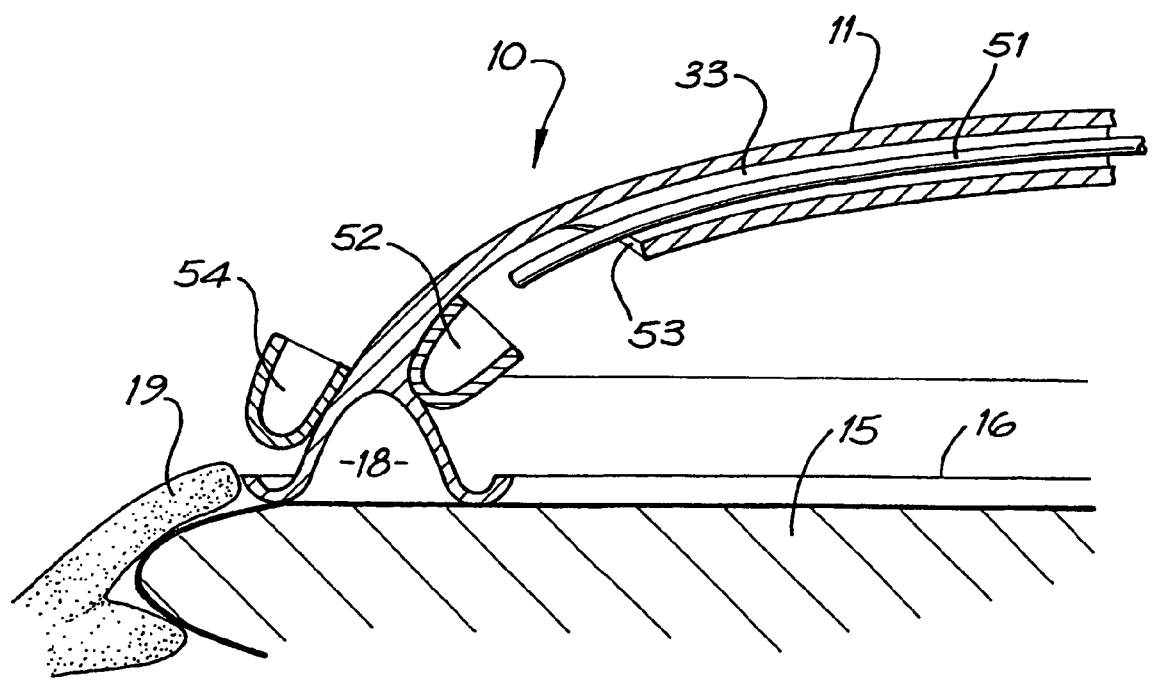
FIG. 5 is a schematic cross section showing an insertion rod.

As shown in FIG. 5, a second tube 33 (see FIGS. 3b to 3d) can be used to temporarily carry an insertion rod 51. Preferably, a small cup 52 or other termination is located within the sleeve 11 and adjacent to the distal opening 53 of the tube 33. The insertion rod 51 allows for convenient insertion and positioning of the device and is fully removed prior to use. The cup 52 admits the tip of the positioning rod 51 and prevents the rod from puncturing the sleeve 11. Once the rod 51 is removed, the tube 33 can be used to carry fluids into or out of the interior space of the sleeve. In the alternative, a cup 54 can be fixed to or integrally moulded with the exterior surface of the sleeve 11 so that the positioning rod 51 can be disposed on the exterior of the sleeve 11. Accordingly, the tube 33 may be positioned on the exterior surface (see FIG. 3b) or other means may be provided to temporarily hold the positioning rod 51 prior to its withdrawal.

Figure 6:
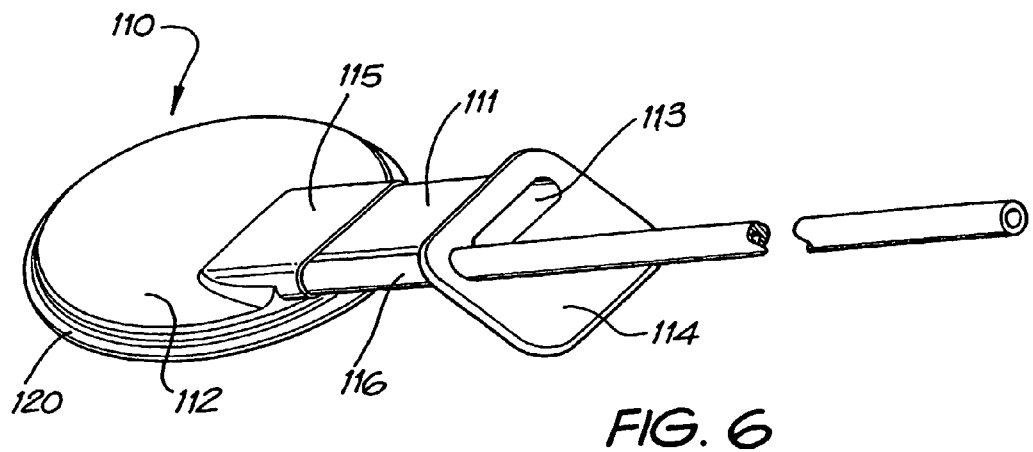
FIG. 6 is a perspective view of a capsule sealing device according to the teachings of the present invention.

As shown in FIG. 6, a capsule sealing device according to another embodiment of the invention comprises a flexible sleeve 111 which terminates in a vacuum platter 112 and opens onto the underside of the platter 12 thereby creating a sealed fluid channel from the underside through the interior of the sleeve. As previously mentioned, the sleeve 111 and the platter 112 are preferably made from silicone or polyurethane or other soft and flexible materials and the internal surface of the sleeve may be coated with a slippery substance such as a hydro gel. The platter 112 and the distal portion of the sleeve 111 to which it is attached at a predetermined angle (in this instance 20°) must be small enough and flexible enough to pass through an incision in a cornea.

Figure 7:
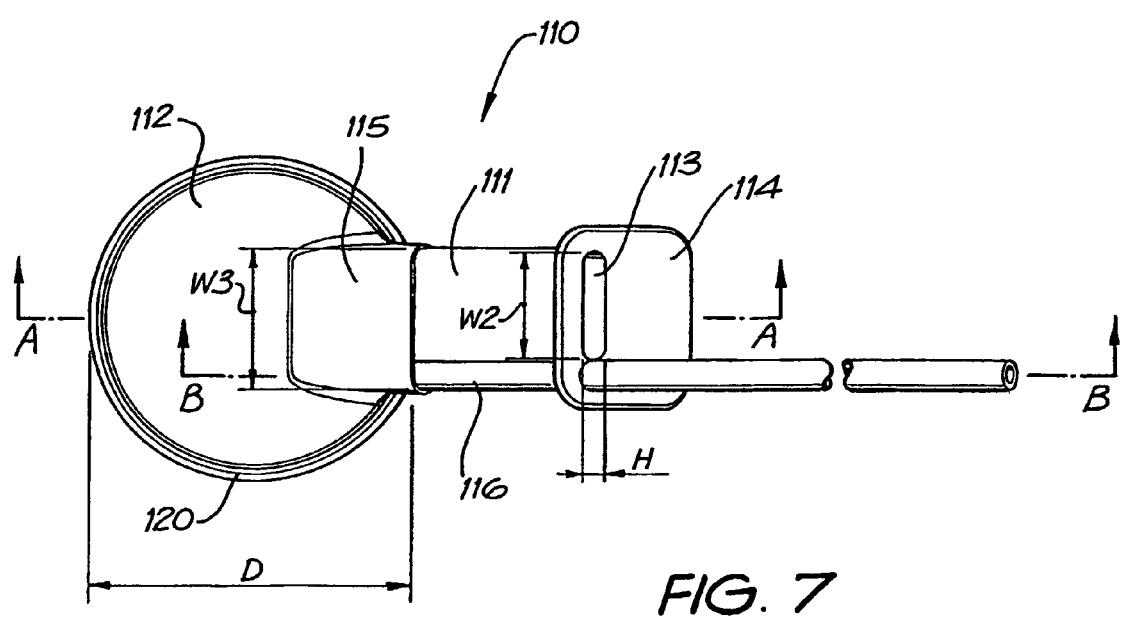
FIG. 7 is a top plan view of the device depicted in FIG. 6.
Figure 8:
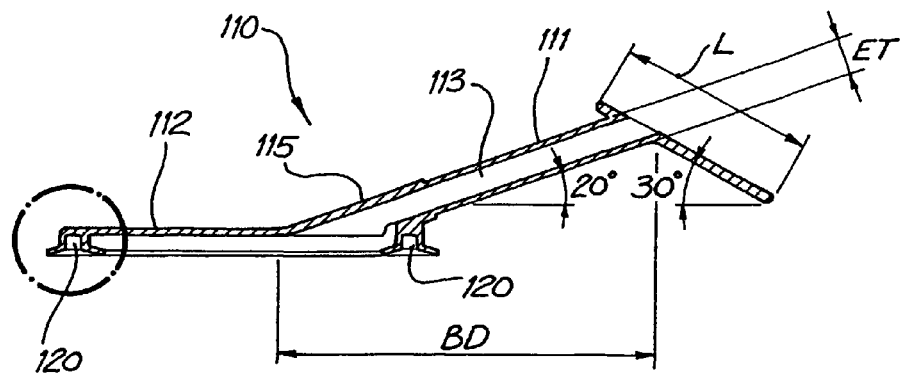
FIG. 8 is a cross-section through line A-A of FIG. 7.

As shown in FIGS. 6 to 8, the sleeve 111 incorporates a suction tube 116 and a throat 113. The throat 113 leads from a rectangular (or other shaped) flange 114 to the underside or interior of the platter 112. The somewhat oversized flange acts as a shield, preventing fluid flowing out of the top of the throat from falling back into the eye. The throat 113 provides a passageway through which instruments or fluids or conduits may access the interior of the capsule through the corneal incision. The sleeve 111 and throat 113 are relatively flat to minimise wound distortion. The join 115 between the sleeve 111 and the platter 112 may be slightly thickened or reinforced to provide extra strength in this area.

Figure 9:
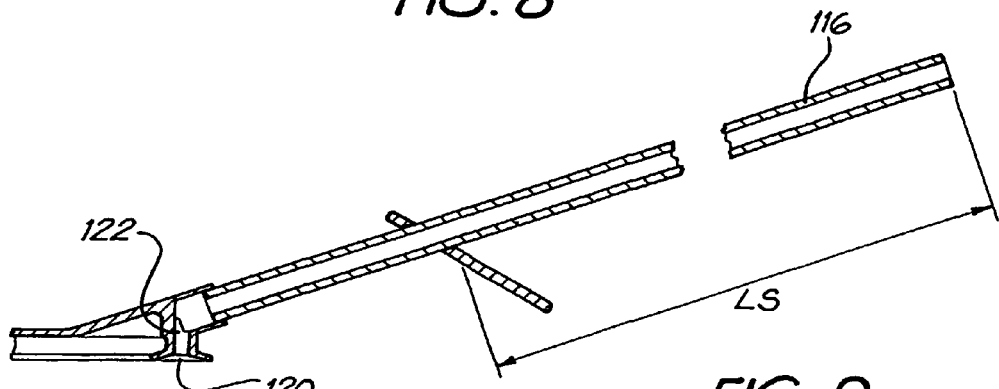
FIG. 9 is a cross-section through line B-B of FIG. 7.

The suction tube 116 is located along one edge of the sleeve 111 and may be moulded into it. The suction tube 116 provides a sealed passageway and fluidic communication with the suction ring or channel 120. The communication between the suction ring or channel 120 and suction tube 116 is shown in FIG. 9. It will be appreciated that the suction tube 116 may be used for a variety of purposes. In one example, the suction tube 116 may serve as a guide for an insertion rod. The throat may also serve this purpose. Such a rod is inserted into the tube 116 for the purpose of manoeuvring the device through a corneal incision and into position on the lens capsule.

Figures 10, 11:
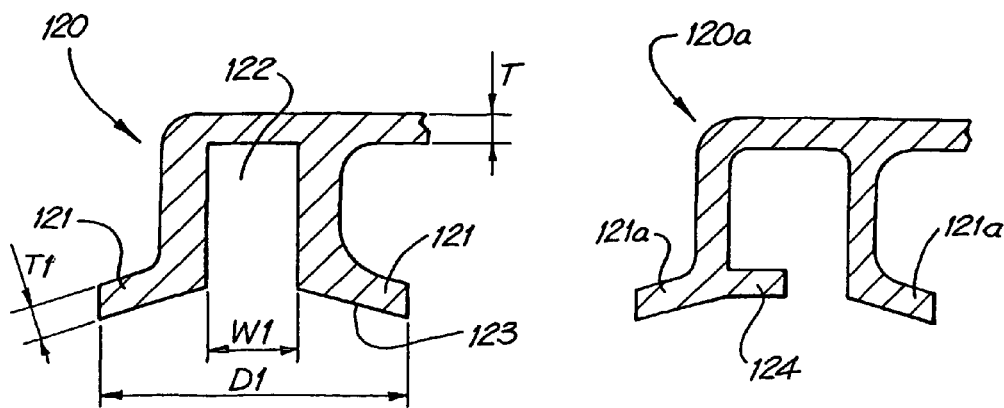
FIG. 10 is a detail of the seal depicted in FIG. 3.
FIG. 11 is a view similar to FIG. 10 of a modified form of seal.

As shown in FIG. 10, the suction ring 120 which acts as a seal and surrounds the platter 112 comprises a pair of concentric flexible lips 121 which surround an annular channel 122. The flat and flexible undersides 123 of the lips 121 allow the platter 112 to adhere to and seal against the lens capsule with the platter 112 surrounding the capsulorhexis. The suction ring 120 thus forms an inverted "U" cross-section about its entire circumference.

It will be appreciated that the suction platter 112 has been disclosed as disc shaped, but may be fabricated as any convenient plan form such as oval, rectangular or irregular to suit any surface shape or confirmation. Likewise, the suction cannel 120 has been disclosed as a ring, bit its primary characteristic is merely that it confirms to the shape of the underside of the suction platter 112, regardless of what shape the platter happens to be.

A modified form of the suction ring 120a is shown in FIG. 11. Apart from outwardly directed lips 121a, the ring 120a has an inwardly lip 124.

So that the invention may be better understood the following dimensions are intended to serve as examples and not as limitations to the scope or spirit of the invention. For example, and with reference to FIGS. 7 to 10, the maximum diameter (D) of the platter is about 7 mm. The length (L) of the flange is about 3.4 mm. The width (W2) of the throat is about 2.35 mm. The height (H) of the throat is about 0.43 mm. The width (W1) of the central channel 122 of the suction ring 120 is about 0.2 mm. The distance (D1) between the inner and outer extremities of the lips 121 is about 1 mm. The thickness (T1) of the lips 121 is about 0.1 mm. The angle of inclination of the lips 121 with respect to a referenced horizontal plain is about 15° on each side. The thickness (T) of the upper surface of the suction disc 112 is approximately 0.1 mm. The sleeve 111 is inclined with respect to a reference horizontal plain by about 20°. As shown in FIG. 8, the flange 114 is inclined by about 30° to a reference horizontal plain. The suction tube 116 extends by a distance (LS) of about 15 mm from the face of the flange 114. The suction tube 116 (which may be insert moulded into the suction disc assembly) has an outside diameter of about 0.63 mm and an inside diameter of about 0.3 mm. As shown in FIG. 8, the baseline distance (BD) between the centre of the platter 112 and the end of the sleeve 111 is about 7.2 mm. The width (W3) of the sleeve 111 is about 3.08 mm. The external thickness (ET) of the sleeve is about 0.63 mm. The wall thickness of the throat is about 0.1 mm.

Figure 12:
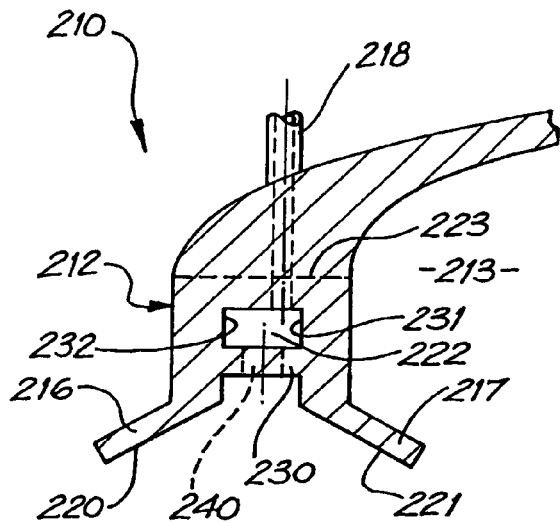
FIG. 12 is a schematic cross sectional view of a first embodiment of the present invention.

FIGS. 12 to 16 are representative of a portion of the cross section of a vacuum sealing device 210 of the general type depicted in FIGS. 1 and 6. As such FIG. 12 corresponds generally to the area A of FIG. 1 and illustrates a close up view of a portion of the platters 12 and 212. In this context the term "ring" is not meant to denote a circular shape to the exclusion of other closed curves. As shown in FIG. 12, the platter 212 further comprises an outer edge 216 and an inner edge 217. The bottom surfaces 220, 221 of the outer and inner edges of the platter 212 form body contacting surfaces of the device 210. A manifold 222 is provided above the body contacting surfaces 220, 221. The manifold defines a chamber which follows the contour of the platter 212 and serves to provide uniform vacuum to the entirety of the platter 212 from a source such as the vacuum tube 218 which leads into the manifold 222. For clarity, the platter or suction ring 212 is shown in FIG. 12 as being separate from the remainder of the device by the imaginary or dotted line 223. This same dotted line 223 is used in FIGS. 13 to 15 to represent the conceptual boundary between the suction channel or ring 212 and the remainder of the device 210.

FIG. 12 depicts a continuous membrane barrier or flange 230 which extends between the inner and outer walls 231, 232 of the manifold 222. In some instances, the conformation of the sealing ring 212 will be circular. However, the suction ring 212 need not be exclusively circular and other conformations are contemplated (see FIG. 18).

In this example, the barrier flange 230 follows the conformation of the suction channel or ring 212 and but for regular or irregularly spaced openings 240 defines a barrier between the body contacting surfaces 220, 221 and the manifold 222. The openings 240 are sized to permit vacuum pressure to be communicated below the barrier flange 230 while at the same time preventing debris from entering the manifold 222.

Figure 13:
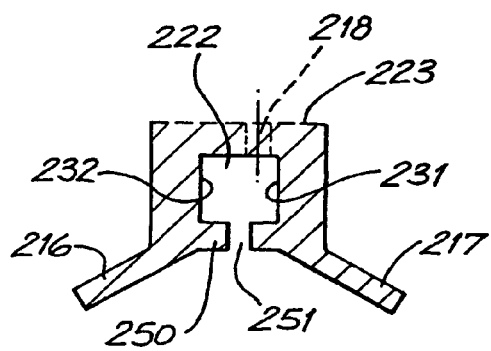
FIG. 13 is a schematic cross sectional diagram illustrating a second embodiment of the present invention.
Figure 14:
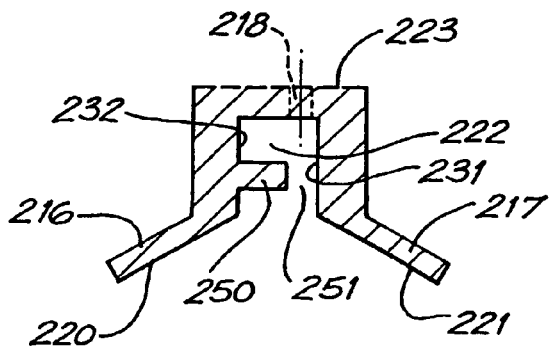
FIG. 14 is a schematic cross sectional diagram illustrating a third embodiment of the present invention.
Figure 15:
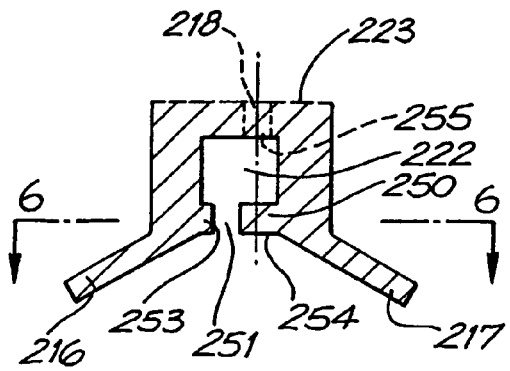
FIG. 15 is a schematic cross sectional diagram illustrating a fourth embodiment of the present invention.

As shown in FIGS. 13 and 15, the baffle or barrier 250 formed within the manifold 222 may be formed along either or both the inner and outer side walls 231, 232 of the manifold 222. As such, the gap 251 which extends into the manifold 22 may be located along either manifold wall 231, 232 or, as suggested by FIG. 14 centrally of the manifold 222. FIG. 14 also illustrates that the barrier 250 may be located at the lower most extent of the manifold 222.

It will be appreciated that the barrier, eg 240, 250 may be provided as a single flange which follows a side wall (FIG. 13), a pair of flanges which define a gap there between (FIG. 14) or as a continuous but perforated membrane which extends between the side walls (FIG. 12).

Figure 16:
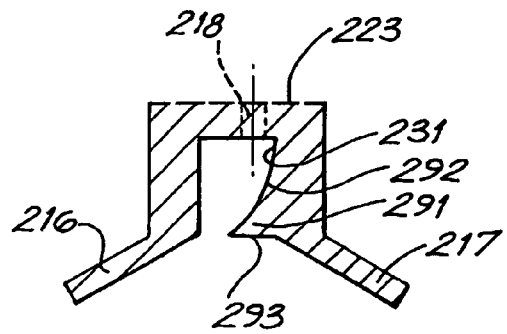
FIG. 16 is a schematic cross sectional diagram illustrating a flange whose upper surface is blended into a manifold.
Figure 17:
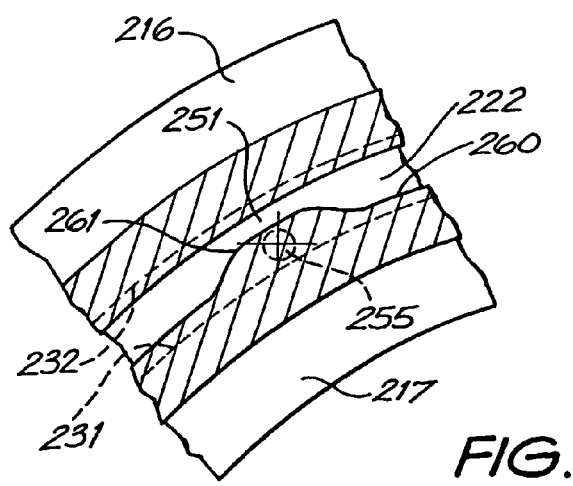
FIG. 17 is a cross section through lines 6-6 of FIG. 14.

FIG. 15 illustrates that a barrier 250 may be comprised of flanges 253, 254 of differing widths. In some embodiments it may be advantageous to provide a flange wide enough to block direct or linear access to the entry port 255 of the vacuum inlet 218. This requires that the entry port 255 and flange 254 be in alignment as depicted in FIG. 16. A variation of this form of alignment is depicted in FIG. 17. In FIG. 17 it can be seen that the width of inner flange 260 (corresponding to flange 254 in FIG. 15) is enlarged only in the area 261 corresponding to the position below the inlet 255.

As shown in FIG. 16, a barrier or flange 291 may be blended 292 into a sidewall 231 rather than project from it like a cantilever. This provides flat bottom 293 with enhanced rigidity.

Figure 18:
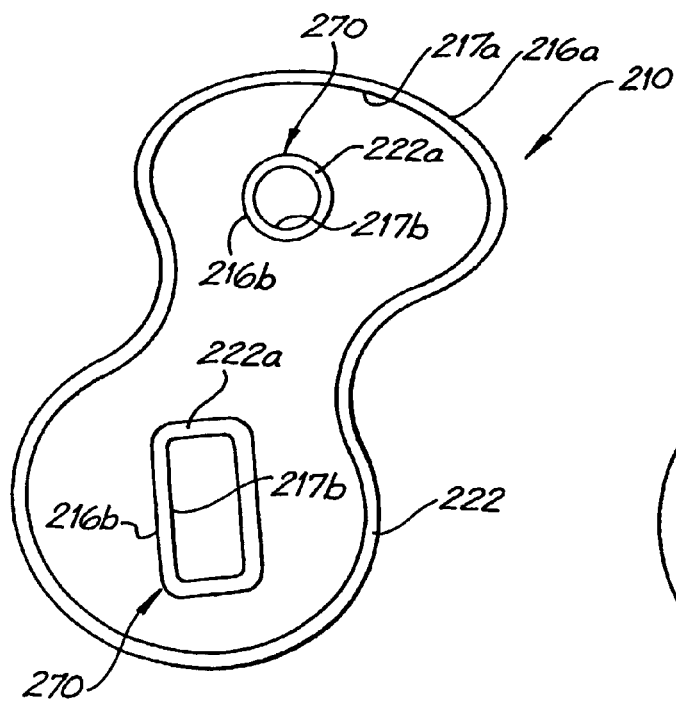
FIG. 18 is a schematic cross sectional view illustrating a complex curvature and an outer peripheral vacuum channel together with a pair of secondary seals which occupy a space within the outer peripheral seal.

As shown in FIG. 18, it will be seen that a vacuum sealing device 210 may be provided with a complex peripheral conformation. As shown in this example, the outer extent of the device 210 is still defined by the vacuum seal created by the inner and outer edges of the suction ring 216a, 217a. However, within the closed curve defined by the inner edge 217a, any number of secondary vacuum seals 270 may be provided. Each of the secondary seals 270 has its own vacuum manifold 222a and each is defined by inner and outer edges of its respective suction ring 216b, 217b. In some embodiments it will be preferential to have the various individual vacuum manifolds controlled separately or in discrete groups. As exemplified by FIG. 17, there are practically no limitations to the shape of the primary or secondary seals within the context of the two dimensional plane.

Figure 19:
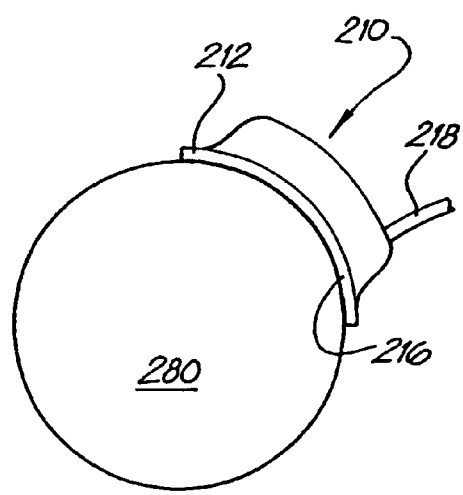
FIG. 19 is an elevation of a vacuum sealing device which is formed such that the peripheral vacuum seal departs from a two dimensional plane.

The invention may also be extended to body contacting sealing surfaces which define shapes in three dimensional space rather than just a two dimensional plane. As shown in FIG. 19, a vacuum sealing device 210 may be manufactured so that the suction ring 212 defines a shape which has body contacting surfaces that depart from a two dimensional plane. In this example, suction ring 212 is shown as having been manufactured to conform to a cylindrical surface 280 although it will be understood that the same illustration may be representative of a vacuum sealing device which is manufactured to conform to e.g. a spherical surface 280.

It will be appreciated that the vacuum sealing device 210 disclosed above may be used on a body surface to limit the application of a fluid (or gas) to a defined area. Once such application is LASEK surgery, where alcohol is applied to the cornea of the eye to loosen the epithelium before laser treatment. A similar device to that disclosed here with an approximate 10 mm inner seal diameter allows alcohol to be delivered via this sealed system and applied to a limited area of the cornea. This limits the risk of the alcohol solution affecting the surrounding ocular tissues.

The invention claimed is:

1. A surgical vacuum sealing device providing a seal about ocular tissues comprising:
a flexible vacuum platter having an underside which has a periphery sized and shaped to surround said ocular tissues, said underside defining a space underneath said flexible vacuum platter;
a vacuum channel formed along said periphery of the platter and connected to a vacuum source to seal the surrounded ocular tissues, said vacuum channel being separated from said space so that connecting said vacuum channel to said vacuum source does not affect fluids in said space, when the surrounded oculat tissues are sealed, and
a sleeve attached to and extending from an exterior surface of the platter, the sleeve having an interior which opens onto said underside, wherein said flexible vacuum platter and said sleeve are soft, flexible, and deformable to fit through a corneal incision.

2. The device of claim 1, wherein:
the sleeve terminates, at a proximal end, in a flange having an opening which leads into the interior of the sleeve.

3. The device of claim 1, wherein:
the vacuum channel further comprises a barrier located within the channel, the barrier being attached to at least one wall inside the channel.

4. The device of claim 1, wherein:
the sleeve has a throat which is flat so as to minimize wound distortion.

5. The device of claim 1, further comprising:
a suction tube in fluid communication with the vacuum channel and is joined to or incorporated into the sleeve.

6. The device of claim 5 wherein:
the suction tube is, along at least a portion, joined to or formed integrally with the sleeve.

7. The device of claim 1, wherein:
the sleeve extends from the exterior surface of the platter at a predetermined angle to allow it to pass through a corneal incision.

8. The device of claim 1, wherein:
the vacuum platter is sized to fit within the margin of a pupil.

9. The device of claim 1, wherein:
the vacuum platter is sized to surround a capsulorhexis.

10. The vacuum sealing device of claim 1, further comprising:
the sleeve having, between a proximal extremity and the distal extremity, an access opening formed therein.

11. The vacuum sealing device of claim 1, further comprising:
a rod which fits within a tube which is formed into or affixed to the sleeve.

12. The vacuum sealing device of claim 1, wherein:
said channel extends continuously around said periphery.

13. The vacuum sealing device of claim 1, further comprising:
at least one additional vacuum channel formed onto the underside of the platter and within the periphery of the underside.

14. The vacuum sealing device of claim 1, wherein:
the sleeve has, between a proximal extremity and the distal extremity an access opening formed in it.

15. A surgical vacuum sealing device providing a seal about ocular tissue comprising:
a flexible plate having a periphery and sized and shaped to form an internal space with the surface of the ocular tissue when placed on the eye;
a sleeve having a distal extremity which terminates in a substantially continuous suction channel formed along said periphery and sized to surround said tissue, said suction channel being separate from and not in fluid communication with said internal space, when the flexible plate is placed on the eye;
the suction channel being in fluid communication with a suction tube to form a seal around the surrounded tissue, wherein said sleeve and the flexible vacuum platter are soft, flexible, and deformable to fit through a corneal incision.

16. The vacuum sealing device of claim 15, wherein:
the sleeve has a throat which is flat so as to minimize wound distortion.

17. The vacuum sealing device of claim 15, wherein:
the sleeve extends from the periphery at a predetermined angle to allow it to pass through a corneal incision.

18. The vacuum sealing device of claim 15, wherein:
the sleeve is sized to fit within the margin of a pupil.

19. The vacuum sealing device of claim 15, wherein:
the periphery is sized to surround a capsulorhexis.

20. The vacuum sealing device of claim 15, further comprising:
at least one auxiliary tube carried within or by the sleeve, said tube having a distal end which terminates in said interior space for the delivery or removal of fluids.

21. The vacuum sealing device of claim 15, wherein:
the sleeve is provided with one or two stabilizing ribs located about an exterior circumference of the sleeve.

22. The vacuum sealing device of claim 15, further comprising:
a positioning rod which fits within an auxiliary tube.

23. The vacuum sealing device of claim 15, further comprising:
a barrier located within the channel, the barrier attached to at least one wall inside the channel.

24. The vacuum seal device of claim 15 wherein:
said sleeve is deformable to fit through an incision in the cornea.

25. A method of performing intraocular surgery using a suction device including a sleeve terminating in a periphery of a plate forming an interior space when placed on ocular tissue, said periphery formed with a circumferential suction channel separated from the interior space comprising:
 making an incision in the cornea;
 inserting said periphery through said incision, wherein said periphery and said sleeve is soft, flexible, and deformable to fit through a corneal incision during insertion;
 deploying said periphery on an eye tissue; and
 applying vacuum to said suction channel to seal an internal portion of said eye tissue, the vacuum being restricted within said channel and not penetrating said interior space.

26. The method of claim 25 further comprising inserting chemical agents through said sleeve, said chemical agents being removed through said suction channel to protect intraocular tissues disposed outside said seal.

* * * * *